(12) United States Patent
Shimokita et al.

(10) Patent No.: US 11,499,961 B2
(45) Date of Patent: Nov. 15, 2022

(54) BODY FLUID OPTICAL ANALYSIS DEVICE

(71) Applicant: GENIAL LIGHT CO., LTD., Hamamatsu (JP)

(72) Inventors: Ryo Shimokita, Hamamatsu (JP); Tatsuyuki Fujita, Hamamatsu (JP); Takashi Sawada, Toyohashi (JP); Taisuke Yamauchi, Kosai (JP)

(73) Assignee: GENIAL LIGHT CO., LTD., Hamamatsu (JP)

( * ) Notice: Subject to any disclaimer, the term of this patent is extended or adjusted under 35 U.S.C. 154(b) by 27 days.

(21) Appl. No.: 16/762,643

(22) PCT Filed: Nov. 13, 2018

(86) PCT No.: PCT/JP2018/042033
§ 371 (c)(1),
(2) Date: May 8, 2020

(87) PCT Pub. No.: WO2019/098207
PCT Pub. Date: May 23, 2019

(65) Prior Publication Data
US 2020/0363395 A1 Nov. 19, 2020

(30) Foreign Application Priority Data

Nov. 14, 2017 (JP) .............................. JP2017-219480
Apr. 13, 2018 (JP) .............................. JP2018-077353

(51) Int. Cl.
*G01N 33/49* (2006.01)
*G01N 21/59* (2006.01)
(Continued)

(52) U.S. Cl.
CPC ......... *G01N 33/4915* (2013.01); *G01N 21/59* (2013.01); *G01N 33/493* (2013.01);
(Continued)

(58) Field of Classification Search
CPC .. G01N 33/4915; G01N 21/59; G01N 33/493; G01N 2201/064; G01N 21/85;
(Continued)

(56) References Cited

U.S. PATENT DOCUMENTS 4,227,814 A * 10/1980 Soodak ............... A61M 1/1692
250/576
4,533,350 A * 8/1985 Danby ................ A61M 5/1689
604/253
(Continued)

FOREIGN PATENT DOCUMENTS

CN 203011824 U 6/2013
GB 2182432 A 5/1987
(Continued)

OTHER PUBLICATIONS

Japan Patent Office, Office Action Issued in Application No. 2018-077353, dated Apr. 6, 2021, 8 pages.
(Continued)

*Primary Examiner* — Michael P LaPage
(74) *Attorney, Agent, or Firm* — Alleman Hall Creasman & Tuttle LLP

(57) ABSTRACT

A body fluid analysis device that irradiates a body fluid in a tube having translucency with light and analyzes the body fluid on the basis of light having passed through the tube is adapted to include: a base; an attachment that is attached to the base 1 so that the tube is pinched in its radial direction between the attachment and the base; a light emitting element that is provided to the base or the attachment; and a light receiving element that is provided to the base or the attachment, in which in a state where the attachment is attached to the base, between the base and the attachment, the light emitting element and the light receiving element are arranged so as to pinch the tube in the radial direction, or
(Continued)

both of the light emitting element and the light receiving element are arranged in the base or the attachment.

11 Claims, 10 Drawing Sheets

(51) Int. Cl.
*G01N 33/493* (2006.01)
*A61M 25/00* (2006.01)
*G01N 21/03* (2006.01)

(52) U.S. Cl.
CPC . *A61M 25/0017* (2013.01); *A61M 2202/0496* (2013.01); *A61M 2205/331* (2013.01); *A61M 2205/3306* (2013.01); *G01N 2021/0364* (2013.01)

(58) Field of Classification Search
CPC ...... G01N 2021/0364; A61M 25/0017; A61M 2202/0496; A61M 2205/3306; A61M 2205/331; A61M 1/367; A61F 5/4405; A61F 5/442; A61F 5/44
See application file for complete search history.

(56) References Cited

U.S. PATENT DOCUMENTS

| | | | | |
|---|---|---|---|---|
| 4,884,065 A * | 11/1989 | Crouse | ......... | A61M 5/365 340/632 |
| 5,102,392 A * | 4/1992 | Sakai | ......... | A61M 5/365 128/DIG. 13 |
| 5,331,958 A * | 7/1994 | Oppenheimer | ...... | G01N 21/532 600/322 |
| 5,565,977 A * | 10/1996 | Rosinko | ......... | G01N 33/491 356/39 |
| 5,672,887 A | 9/1997 | Shaw et al. | | |
| 7,726,174 B2 * | 6/2010 | Riley | ......... | G01N 29/222 73/19.03 |
| 8,986,252 B2 * | 3/2015 | Cummings | ......... | A61M 5/14232 417/477.2 |
| 9,402,987 B2 * | 8/2016 | Kamen | ......... | F16K 7/06 |
| 2003/0168059 A1 * | 9/2003 | Pacey | ......... | A61B 1/267 128/207.14 |
| 2008/0134750 A1 * | 6/2008 | Riley | ......... | A61M 1/3626 73/19.03 |
| 2010/0160751 A1 | 6/2010 | Hete et al. | | |
| 2012/0062869 A1 | 3/2012 | Bado et al. | | |
| 2012/0327404 A1 * | 12/2012 | Olesen | ......... | G01N 21/05 422/547 |
| 2013/0317408 A1 * | 11/2013 | Schade | ......... | A61B 5/6866 604/4.01 |
| 2016/0069803 A1 | 3/2016 | Sano et al. | | |
| 2018/0180541 A1 * | 6/2018 | Sano | ......... | G01N 21/59 |

FOREIGN PATENT DOCUMENTS

| | | |
|---|---|---|
| JP | S6378257 U | 5/1988 |
| JP | H07301630 A | 11/1995 |
| JP | 2002156376 A | 5/2002 |
| JP | 2009300337 A | 12/2009 |
| JP | 2012040058 A | 3/2012 |
| JP | 2017104578 A | 6/2017 |
| TW | 201341779 A | 10/2013 |
| WO | 2014170985 A1 | 10/2014 |

OTHER PUBLICATIONS

European Patent Office, Extended European Search Report Issued in Application No. 18878396.3, dated Jul. 8, 2021, Germany, 13 pages.
Japan Patent Office, Decision of Refusal Issued in Application No. 2018-077353, dated Jul. 13, 2021, 9 pages.
ISA Japan Patent Office, International Search Report Issued in International Application No. PCT/JP2018/042033, dated Feb. 12, 2019, WIPO, 4 pages.
Taiwan Intellectual Property Office, Office Action and Search Report Issued in Application No. 107140389, dated Jul. 4, 2022, 13 pages.

* cited by examiner

BODY FLUID OPTICAL ANALYSIS DEVICE

TECHNICAL FIELD

The present invention relates to a body fluid analysis device that irradiates a body fluid in a tube having translucency with light and analyzes the body fluid on the basis of light having passed through the body fluid.

BACKGROUND ART

For example, there may be a case where a balloon catheter is placed in the urinary bladder of a patient to be subjected to surgery under general anesthesia or of a patient who cannot move out of a bed for a long period of time, and urine withdrawn from the inside of the urinary bladder is accumulated in a urine bag. Such a urine bag (a uro-bag) includes: a urine guide tube connected to the outside end part of the balloon catheter; an accumulation part that is connected to the urine guide tube to accumulate urine; and an outlet tube for draining a certain amount of urine accumulated in the accumulation part to the outside for disposal (see Patent Literature 1).

Meanwhile, when a balloon catheter is placed in the urinary bladder, in particular, in the case of a patient with compromised immunocompetence, the urinary bladder or the kidneys connected to the urinary bladder may be inflamed by bacterial infection or the like. For this reason, in order to confirm whether the urinary bladder is functioning normally, the urine volume and the degree of occult blood in urine are checked by a nurse.

However, regarding the degree of occult blood, the nurse has to visually compare urine color with a six-stage color chart to determine whether the blood color may be left as-is, the blood color is non-problematic even when only the nurse provides care, or the blood color requires medical intervention, which can be performed only by a doctor.

In particular, the difference in urine color between when only a nurse can provide care and when the medical intervention by a doctor is required is very subtle, and there is a case where it is difficult for a nurse to determine which is the case. For example, if a doctor is allowed to be always called in an obscure case, the doctor devotes him/herself to a patient whom the doctor is not supposed to be responsible for, and valuable medical resources may be wasted, such as being unable to take care of another critically ill patient. On the other hand, if only a nurse provides care when medical intervention by a doctor is required, the patient's condition may be worsened.

CITATION LIST

Patent Literature

Patent Literature 1
Japanese Unexamined Patent Publication JP-A2002-156376

SUMMARY OF INVENTION

Technical Problem

The present invention has been made in consideration of the problems as described above, and intends to provide a body fluid analysis device that makes it possible to more accurately analyze a body fluid such as urine than visual inspection to, for example, reduce the burden on medical professionals.

Solution to Problem

That is, the body fluid analysis device according to the present invention is a body fluid analysis device that irradiates a body fluid in a tube having translucency with light and analyzes the body fluid on the basis of light having passed through the tube, and the body fluid analysis device includes: a base; an attachment that is attached to the base so that the tube is pinched in its radial direction between the attachment and the base; a light emitting element that is provided to the base or the attachment; and a light receiving element that is provided to the base or the attachment, in which in a state where the attachment is attached to the base, between the base and the attachment, the light emitting element and the light receiving element are arranged so as to pinch the tube in the radial direction, or both of the light emitting element and the light receiving element are arranged together in one of the base and the attachment.

Here, the body fluid refers to a concept including not only various types of fluids that organisms have in their bodies but also secretory fluids.

In such a configuration, by only attaching the tube so that it is pinched by the base and the attachment, the light emitting element and the light receiving element can be positioned in positions suitable for measuring the body fluid.

Further, by interposing the tube between the base and the attachment, the light emitting element or the light receiving element can be separated by a predetermined distance or brought into a predetermined contact state with respect to the outer surface of the tube. For this reason, an optical system suitable for reducing effects when the light passes through the tube and other effects due to stray light and for sufficiently detecting the light having passed through the body fluid can be reproducibly achieved. Accordingly, even when a nurse unfamiliar with the assembly of an optical system or machinery, or the like attaches the base and the attachment to the tube, an equipment error is unlikely to occur when analyzing the body fluid.

For these reasons, the body fluid in the tube can be accurately analyzed based on the light detected by the light receiving element even in a non-contact manner, and for example, it becomes possible to automate the determination of the degree of occult blood, or the like, which has been visually determined by a nurse, making it possible to significantly reduce the burden at medical sites.

In addition, the present invention makes it possible to retrofit the body fluid analysis device to a tube through which a body fluid circulates in existing medical equipment or the like and optically analyze the body fluid flowing through or retained in the tube.

In order to make it difficult for the tube to move in its extending direction or circumferential direction to continuously analyze the body fluid at the same position and to make the contact state or separation distance between the light emitting element or the light receiving element and the outer surface of the tube suitable for analyzing the body fluid, it is only necessary that the attachment includes a contact surface in contact with an outer surface of the tube, and the tube is configured to be pressed against the base in the state where the attachment is attached to the base.

In order to bring the light emitting element or the light receiving element into contact with the outer surface of the tube to reduce the occurrence or detection of stray light due to the tube, it is only necessary that the attachment is configured so that at least a part of the light emitting element or the light receiving element is substantially flush with the contact surface.

A tube that is used for medical equipment and through which a body fluid circulates may bend. Even in such a case, in order to fix the tube in a predetermined position or direction only by interposing the tube between the base and the attachment, and to make it easy to create a state suitable for making the light get to the light receiving element from the light emitting element to achieve accurate body fluid analysis, it is only necessary that the base includes a groove into which the tube is fitted, and a through-hole for allowing light emitted from the light emitting element to pass is formed in the bottom part of the groove.

In order to easily align the light axis of the light emitting element with the light receiving element, it is only necessary that the base includes an accommodation part into which the attachment is fitted, and the light receiving element is configured to be arranged on the light axis of the light emitting element in a state where the attachment is fitted into the accommodation part.

In order to make it difficult for the light receiving element to detect outside light other than the light emitted from the light emitting element to further improve the analysis accuracy of the body fluid, it is only necessary that the base includes: a main body part to which the attachment is attached; and a protrusion part that protrudes outward from the main body part along the extending direction of the groove and is formed with a part of the groove, and a cover that is configured to cover at least the protrusion part of the base is further included.

In order to make it possible for the attachment to be pressed against the outer surface of the tube with a predetermined force to achieve a contact state ideal for analyzing the body fluid, it is only necessary that an engagement structure formed between the base and the cover is further included, the cover is configured to cover the main body part of the base and the attachment attached to the main body part of the base, and the cover is configured to press the attachment against a base side in a state where the cover is engaged with the base by the engagement structure.

In order to make it possible to temporarily retain the body fluid between the light emitting element and the light receiving element to enable the light to pass through the body fluid for analysis even when the volume of the body fluid flowing through the tube is small, it is only necessary that the groove is curvedly formed.

Specific configurations for making it easy to temporarily retain the body fluid in the body fluid analysis device when analyzing the body fluid flowing through the tube include one in which the groove is formed so as to be downwardly convex in the vertical direction in a use state where the light receiving element is made to receive the light having passed through the tube.

In order to make it easy for the body fluid to be present on the light axis of the light emitting element and make it hard to cause a state where nothing is analyzed, it is only necessary that the groove is formed so as to have an apex in the vicinity of the light axis of the light emitting element in the main body part.

The body fluid analysis device in which urine flows through the tube and that further includes a urine analysis part that analyzes the urine on the basis of the output of the light receiving element makes it possible to accurately and automatically continue to detect the condition of urine of a patient in which a balloon catheter is placed in the urinary bladder, such as the degree of occult blood. Accordingly, not only treatment suitable for the condition of the patient can be appropriately performed, but for example, medical resources can be efficiently managed.

As one of specific embodiments of the body fluid analysis device according to the present invention, one in which blood flows through the tube and that further includes a blood analysis part that analyzes the blood on the basis of the output of the light receiving element can be cited. For example, the condition of blood circulating in an artificial dialysis device, such as a hematocrit value, can be measured during dialysis in a non-contact manner to more accurately control the condition of the blood.

Advantageous Effects of Invention

As described, according to the body fluid analysis device according to the present invention, by attaching the attachment to the base, the tube can be pinched between the base and the attachment to bring the space between the light emitting element and the light receiving element into a state suitable for the light receiving element to acquire light necessary to analyze the body fluid. Accordingly, the body fluid in the tube can be accurately analyzed on the basis of the light, and therefore even in the case of an index that is hard for a person to determine, such as the degree of occult blood, accurate classification of condition can be automated.

LIST OF REFERENCE CHARACTERS

Figure 1:
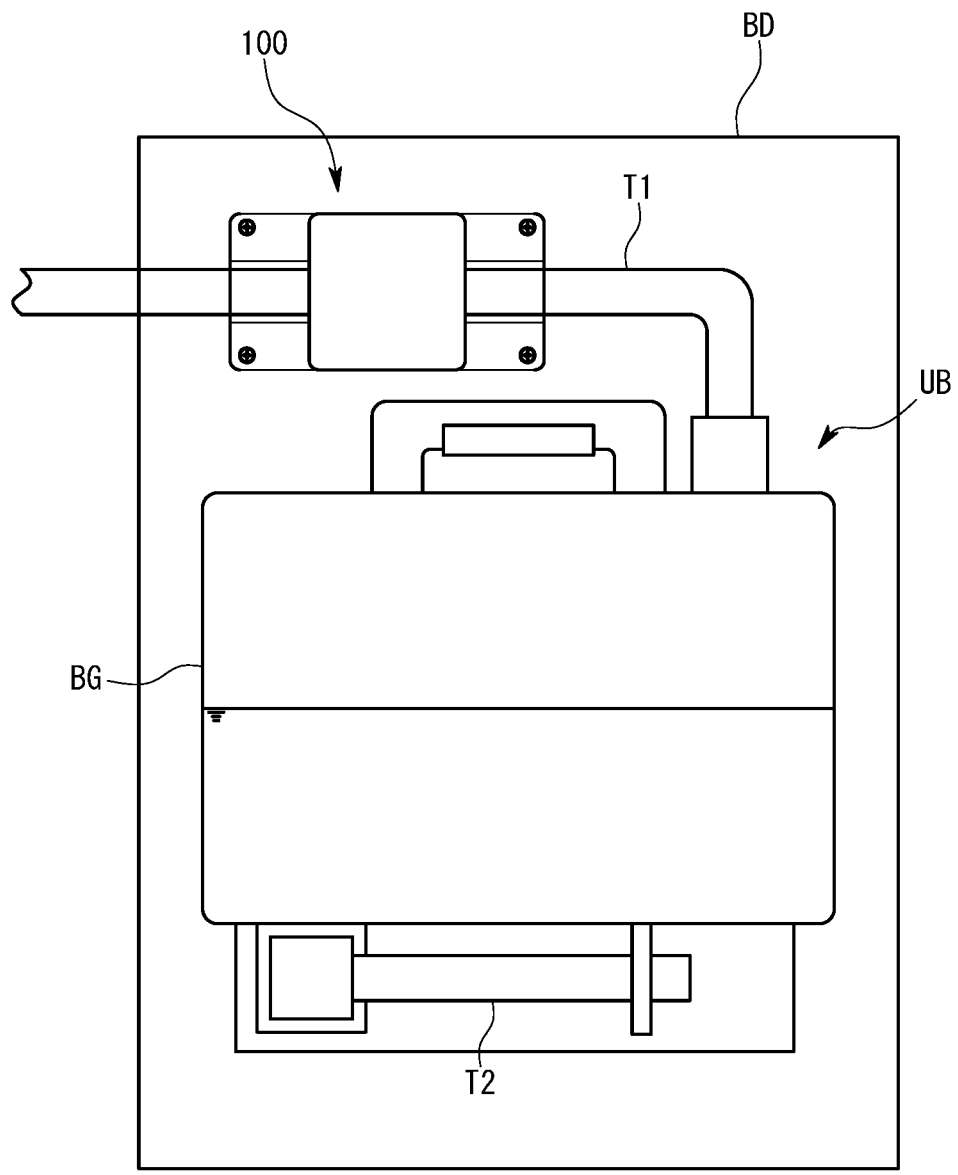
FIG. 1 is a schematic diagram illustrating a state where a body fluid analysis device according to a first embodiment of the present invention is attached to a urine bag.

100 Body fluid analysis device
1 Base

10 Groove
11 Main body part
12 Protrusion part
13 Accommodation part
14 Accommodation part bottom surface
15 Through-hole
L Light emitting element
2 Attachment
21 Contact surface
22 Peripheral side surface
3 Cover
31 Pressing part
32 Shielding part
D Light receiving element
UB Urine bag
T1 Urine guide tube
T2 Outlet tube
BG Accumulation part

DESCRIPTION OF EMBODIMENTS

A body fluid analysis device 100 according to a first embodiment of the present invention will be described with reference to FIG. 1 to FIG. 5. As illustrated in FIG. 1, the body fluid analysis device 100 of the first embodiment is, for example, one that is attached to a urine bag UB for accumulating urine withdrawn from a balloon catheter placed in the urinary bladder of an inpatient and analyzes the condition of the urine circulating through a tube. Here, the urine bag UB is one including: a urine guide tube T1 connected to the end part of the balloon catheter, which is outside the body of the patient; an accumulation part BG in which the urine passing through the urine guide tube T1 is accumulated; and an outlet tube T2 for draining the accumulated urine from the accumulation part BG to the outside. In addition, the urine guide tube T1, the accumulation part BG, and the outlet tube T2 are formed of a transparent resin having translucency, and configured so that the inside urine can be visually inspected. Also, the urine guide tube T1 and the outlet tube T2 are configured as cylindrical tubes having translucency.

In the first embodiment, the body fluid analysis device 100 is attached to the urine guide tube T1, and configured to irradiate the urine circulating through or retained in the urine guide tube T1 with light, and on the basis of the resulting transmitted light, automatically determine, for example, the degree of occult blood.

Figure 2:
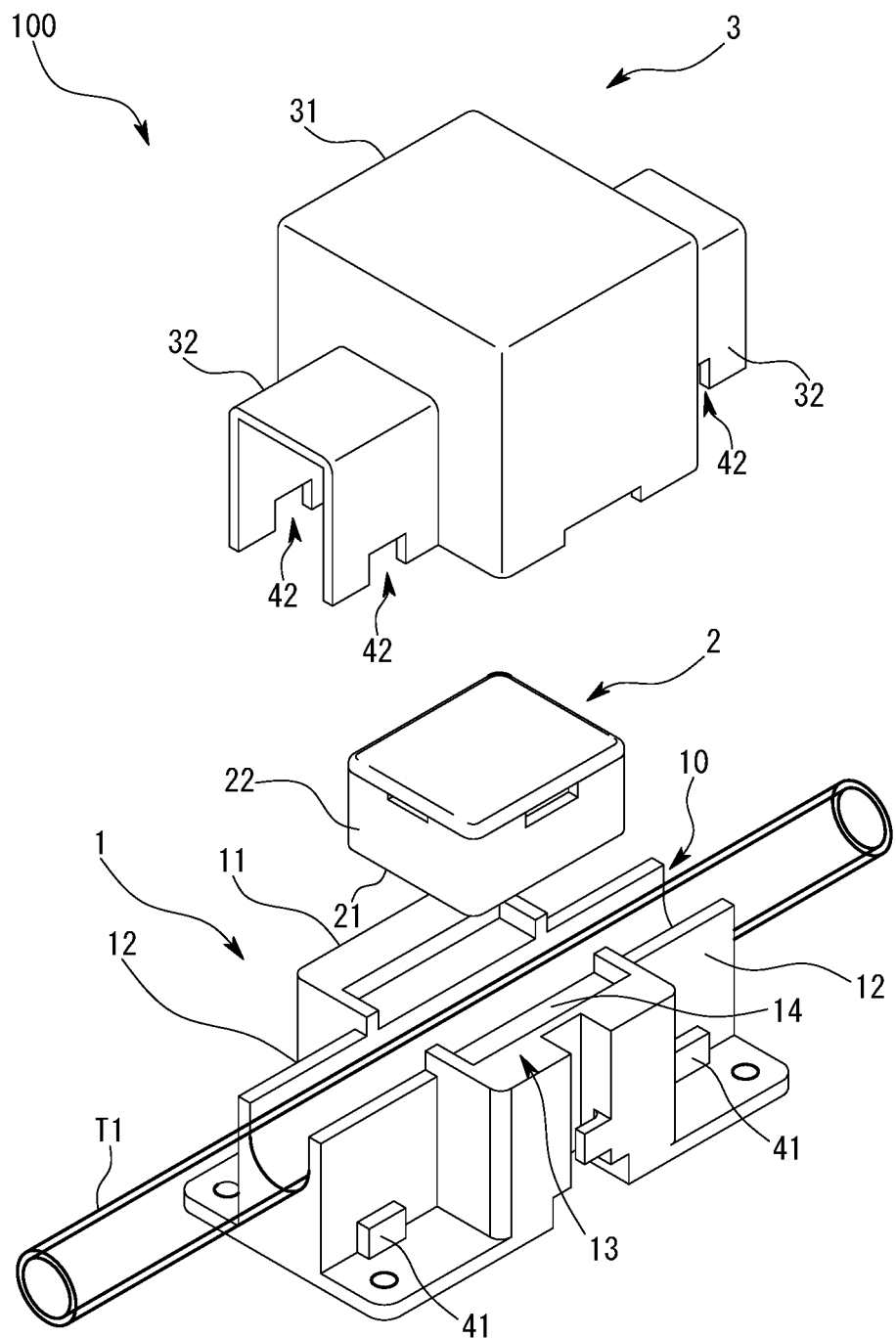
FIG. 2 is a schematic exploded perspective view of the body fluid analysis device according to the first embodiment of the present invention.
Figure 3:
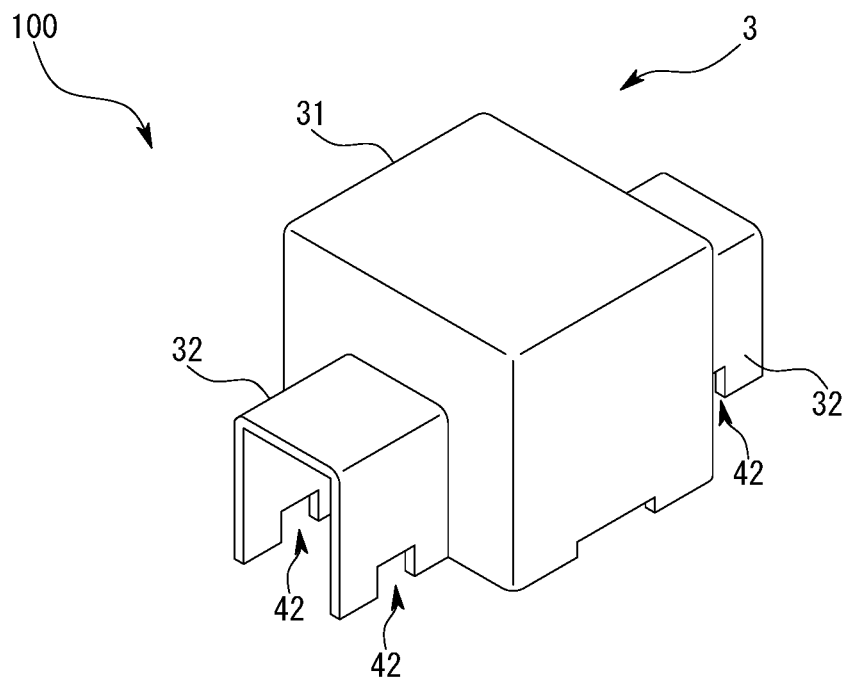
FIG. 3 is a schematic perspective view illustrating a state where an attachment is attached to a base of the body fluid analysis device according to the first embodiment of the present invention.
Figure 3:
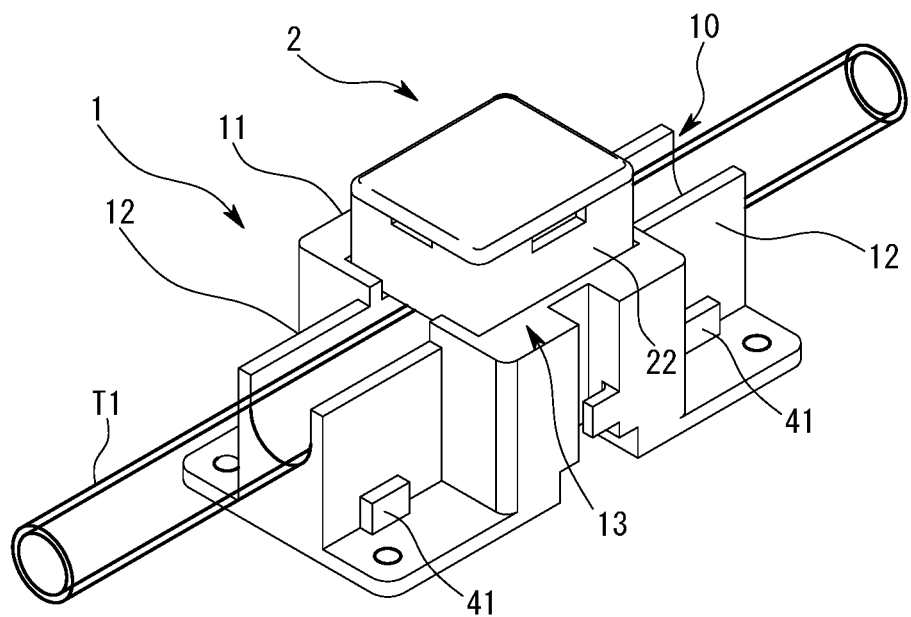
Figure 4:
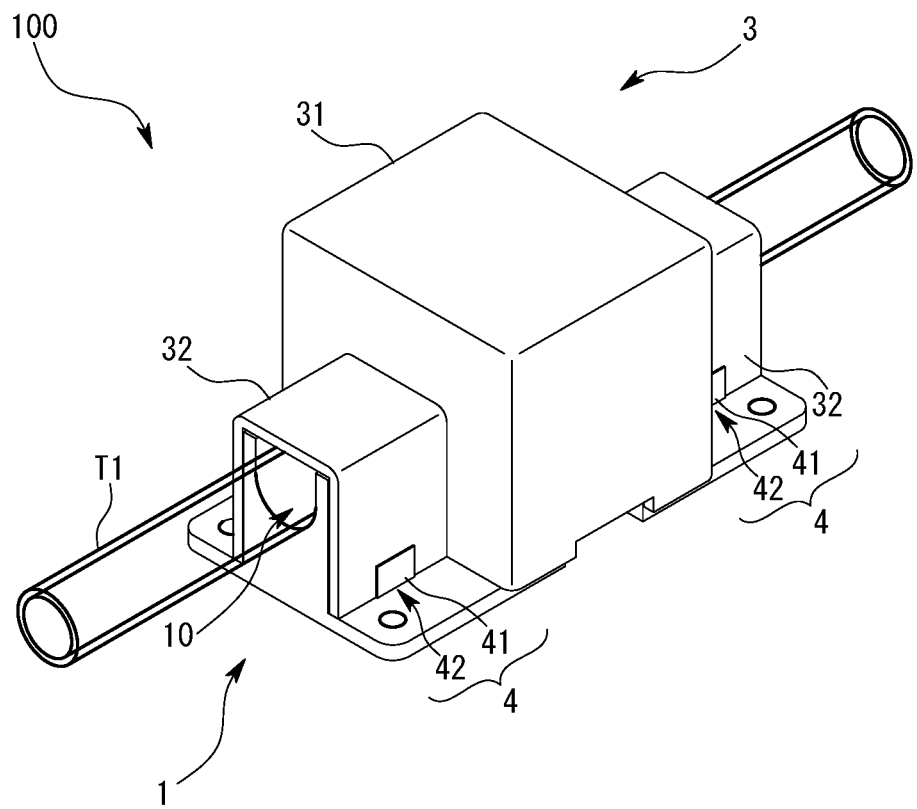
FIG. 4 is a schematic perspective view illustrating a state where the body fluid analysis device according to the first embodiment of the present invention is assembled.
Figure 5:
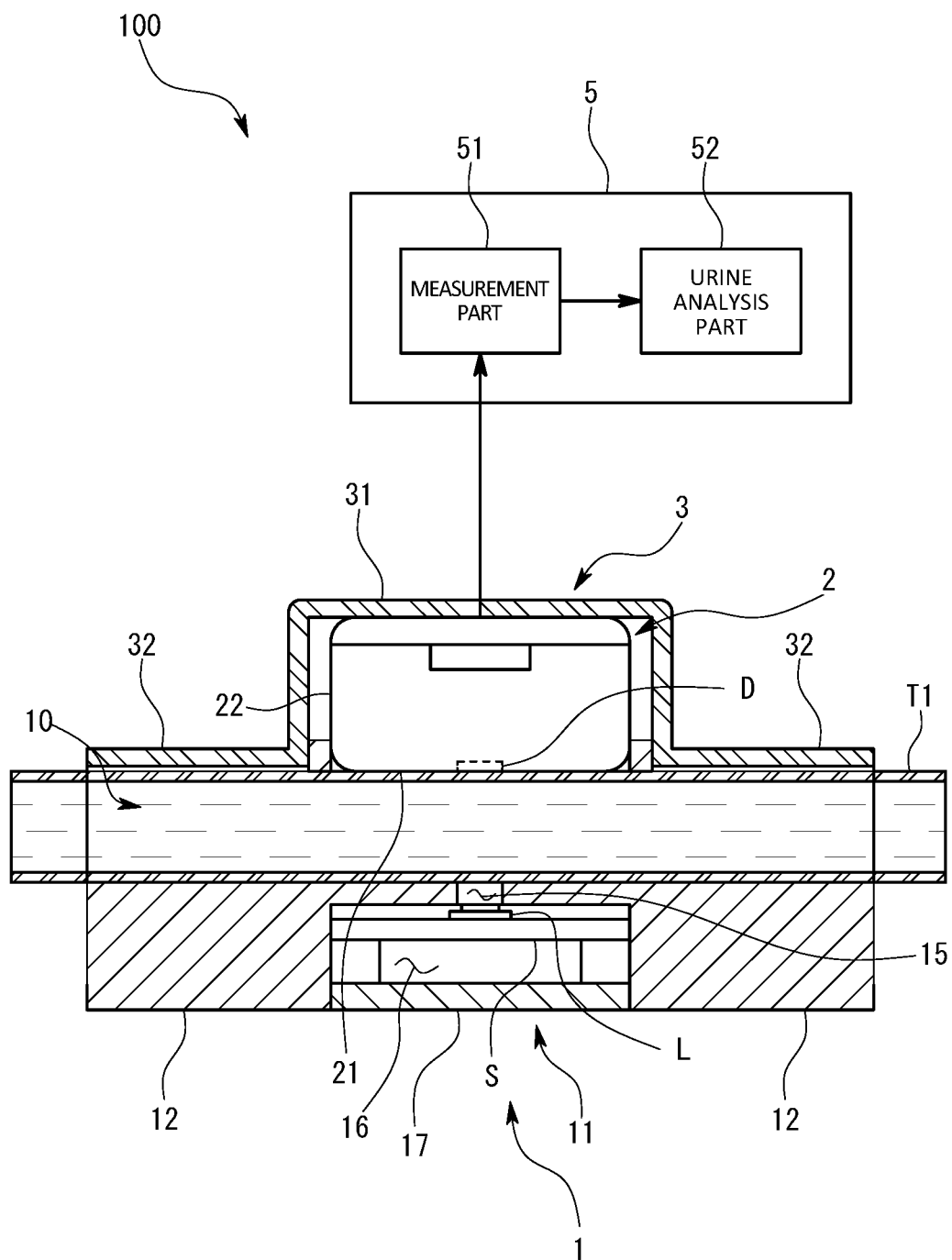
FIG. 5 is a schematic cross-sectional view of the body fluid analysis device according to the first embodiment of the present invention and a functional block diagram.

As illustrated in FIG. 2 to FIG. 5, the body fluid analysis device 100 includes: a base 1 provided with a light emitting element L; an attachment 2 provided with a light receiving element D and attached to the base 1; a cover 3 that covers the base 1 attached with the attachment 2; and an analyzer 5 that analyzes the urine on the basis of the output of the light receiving element D. As illustrated in FIG. 3 and FIG. 5, it is configured so that, in a state where the attachment 2 is attached to the base 1, the urine guide tube T1 as a tube is pinched, and also the light emitting element L and the light receiving element D face each other via the urine guide tube T1. Here, the light emitting element L is, for example, a chip type LED, and the light receiving element D is a photodiode. Also, the base 1 is fixed by screwing to a board BD on which the urine bag UB is hung.

As illustrated in FIG. 2 and FIG. 5, the base 1 includes a linearly extending groove 10 into which the urine guide tube T1 is fitted in a state of being stretched straight. Also, the base 1 includes: a main body part 11 formed with an accommodation part 13 in which the attachment 2 is fitted and accommodated; and two protrusion parts 12 protruding from the main body part 11 toward both sides in the extending direction of the groove 10.

The groove 10 passing through the main body part 11 and the two protrusion parts 12 is such that the width dimension thereof is made substantially the same as the outside diameter of the urine guide tube T1 and the depth dimension thereof is made substantially the same as the outside diameter of the urine guide tube T1 or made slightly smaller than the outside diameter of the urine guide tube T1. That is, when fitting the urine guide tube T1 into the groove 10, the outer surface of the urine guide tube T1 protruding out of the opening side of the groove 10 is made substantially flush with the bottom surface of the accommodation part 13 or made to slightly protrude outward.

As illustrated in FIG. 3, the accommodation part 13 formed on the upper side of the main body part 11 is a recess part formed to have substantially the same dimensions as the outside dimensions of the attachment 2, and adapted so that the peripheral side surfaces 22 of the attachment 2 are fitted to the inner wall surfaces thereof. In the first embodiment, the height dimension of the vertical walls of the accommodation part 13 is set to approximately one third of the height dimension of the attachment 2, and only the bottom surface side of the attachment 2 in which the light receiving element D is provided is accommodated, whereas the top surface side of the attachment 2 is arranged outside the accommodation part 13. Also, the end surfaces of the vertical walls forming the inner wall surfaces of the accommodation part 13 are formed to be flush with the side surface of the groove 10. That is, as viewed in the extending direction of the urine guide tube T1, the vertical walls forming the accommodation part 13 are adapted to prevent outside light from the opening side from entering toward the central side of the main body part 11.

Also, as illustrated in the cross-sectional view of FIG. 5, the central part of the bottom surface of the groove 10 formed in the main body part 11 is formed with a through-hole 15 for allowing light emitted from the light emitting element L contained inside the main body part 11 to pass. On the bottom surface side of the base 1, a housing space 16 in which the light emitting element L, and a substrate S mounted with the light emitting element L and a drive circuit for it are housed is formed, and the housing space 16 is closed by a cover body 17. Also, the light emitting element L is arranged in the housing space 16 so that the light emitting surface thereof faces the through-hole 15. As the wavelengths of the light emitted from the light emitting element L, for example, ones suitable for absorption spectrometry are selected, and a single wavelength or multiple wavelengths is also usable.

As illustrated in FIG. 2 to FIG. 5, the attachment 2 is one of a substantially rectangular parallelepiped shape, and in the center of the bottom surface, the light receiving element D is provided. As illustrated in FIG. 5, the bottom surface of the attachment 2 is a contact surface 21 in contact with an accommodation part bottom surface 14 of the base 1 and the outer surface of the urine guide tube T1, and the light receiving surface of the light receiving element D is made flush with the contact surface 21. Accordingly, in the state where the attachment 2 is attached to the base 1, the contact surface 21 and the light receiving surface of the light receiving element D bring the urine guide tube T1 into a state of being pressed against the bottom of the groove 10 of the base 1. Also, the light receiving element D is in a state of being in contact with the outer surface of the urine guide tube T1. The attachment 2 is provided with a micro USB terminal or the like connected to the internal substrate attached with the light receiving element D inside thereof, and configured to be able to perform power feeding to the light receiving element D, acquisition of the output, or the like. Regarding the light receiving element D, for example, the wavelength band of light that can be received corresponding to the wavelengths of the light emitted from the light emitting element L is set. In contrast, the light receiving element D may be configured to be able to receive only light having a single wavelength.

The cover 3 has a shape corresponding to the base 1, and as illustrated in FIG. 3 and FIG. 4, is attached so that both the base 1 and the attachment 2 attached to the base 1 are entirely covered from the top surface side. The cover 3 includes: a pressing part 31 that covers the main body part 11 of the base 1 and presses the attachment 2 against the base 1; and shielding parts 32 that cover the protrusion parts 12 of the base 1 and prevent the outside light from being incident on the light receiving element D in the attachment 2 attached to the main body part 11 of the base 1.

As illustrated in FIG. 2 to FIG. 5, between the base 1 and the attachment 2, engagement structures 4 are formed and configured so that when the cover 3 is attached to the base 1, the cover 3 presses the attachment 2 against the base 1 to keep a state where the urine guide tube T1 is pinched. That is, the engagement mechanisms 4 each includes an engagement protrusion 41 formed on the base 1 and an engagement recess part 42 formed in the cover 3, and the engagement protrusion 41 and the engagement recess part 42 engage with each other to thereby fix the cover 3 to the base 1. In this embodiment, paired engagement protrusions 41 and paired engagement recess parts 42 are respectively provided on the two outer surfaces of each of the protrusion parts 12 and in the two side surfaces of each of the shielding parts 32.

In a state where the cover 3 is attached to the base 1, the light receiving element D is pressed against the outer surface of the urine guide tube T1 and fixed into the groove 10 of the base 1. For this reason, the light receiving element D is arranged on the light axis of the light emitting element L, and the light receiving element D is in contact with the outer surface of the urine guide tube T1, thus achieving a state suitable for receiving light necessary to analyze the urine. Also, the urine guide tube T1 comes into the state of being pinched between the base 1 and the attachment 2, and therefore the urine guide tube T1 can be prevented from being displaced with respect to the extending direction thereof, making it possible to analyze the urine at the same position of the urine guide tube T1.

The analyzer 5 is configured to acquire the output of the light receiving element D by wire or wirelessly and to determine the degree of occult blood in the urine. More specifically, the analyzer 5 is, for example, one whose functions are implemented by a so-called computer including a central processing unit (CPU), memory, A/D and D/A converters, and other input/output means. The analyzer 5 fulfills functions as at least a measurement part 51 and a urine analysis part 5 as illustrated in FIG. 5 in such a manner that an analysis program stored in the memory is executed and various types of equipment cooperate.

The measurement part 51 is one that, on the basis of an A/D converted output from the light receiving element D, converts it to the amount of received light.

A urine analysis part 52 is one that, on the basis of the light amount obtained by the measurement part 51, calculates a hematocrit value and determines the degree of occult blood from the hematocrit value. Specifically, the urine analysis part 52 determines that, for example, when the hematocrit value is less than 0.1%, the degree of occult blood is Level 0 (Lv. 0); when the hematocrit value is 0.1% or more and less than 0.5%, it is Level 1 (Lv. 1); when the hematocrit value is 0.5% or more and less than 1.0%, it is Level 2 (Lv. 2); when the hematocrit value is 1.0% or more and less than 3.0%, it is Level 3 (Lv. 3); when the hematocrit value is 3.0% or more and less than 10.0%, it is Level 4 (Lv. 4); and when the hematocrit value is 10.0% or more, it is Level 5 (Lv. 5). The urine analysis part 52 may determine the degree of occult blood constantly or at predetermined time intervals.

According to the body fluid analysis device 100 configured as described, only by attaching the urine guide tube T1 in such a manner as to pinch it between the base 1 and the attachment 2, the light emitting element L and the light receiving element D can be positioned in positions suitable for urine measurement.

Further, by interposing the urine guide tube T1 between the base 1 and the attachment 2, a predetermined contact state of the light receiving element D with the outer surface of the urine guide tube T1 can be achieved. For this reason, effects when the light passes through the urine guide tube T1 can be reduced to reproducibly achieve an optical system suitable for sufficiently detecting the light having passed. Accordingly, even when a nurse unfamiliar with the assembly of an optical system or machinery, or the like attaches the base 1 and the attachment 2 with respect to the urine guide tube T1, an equipment error is unlikely to occur.

Also, the base 1 includes: the main body part 11 in which the optical system including the light emitting element L and the light receiving element D is configured; and the two protrusion parts 12 protruding outward from the main body part 11, and the cover 3 is attached so as to cover both of the main body part 11 and the protrusion parts 12, thus making it possible to prevent the outside light from being incident on the main body part 11 side from the protrusion parts 12. Further, parts of the urine guide tube T1 exposed to the outside light can be separated from the main body part 11 by the protrusion parts 12, and for example, even if the light is incident into the resin configuring the urine guide tube T1 at an incident angle satisfying the total reflection condition, the light sufficiently attenuates until it reaches the main body part 11, making it impossible to substantially detect it at the light receiving element D as well.

For these reasons, the degree of occult blood in the urine inside the urine guide tube T1 can be accurately analyzed based on light detected by the light receiving element D even in a non-contact manner. Accordingly, it becomes possible to automate the determination of the degree of occult blood, or the like, which has been visually determined by a nurse, making it possible to significantly reduce the burden at medical sites.

In addition, by retrofitting the body fluid analysis device 100 of the first embodiment to the urine bag UB, which is not supposed to have a role as a measuring instrument, it does not only simply accumulate urine, but can be added with a function as medical equipment for controlling the urinary organs of a patient, such as the urinary bladder. Since the body fluid analysis device 100 can be retrofitted to the urine bag UB as described, it can be used without changing each type of urine bag UB used by each hospital.

Next, a body fluid analysis device 100 according to a second embodiment of the present invention will be described with reference to FIG. 6 to FIG. 8. In addition, members corresponding to the members described in the first embodiment will be marked with the same reference signs.

The body fluid analysis device 100 of the second embodiment is one that is attached to, for example, a blood transport tube T3 that is a tube through which blood to be dialyzed in an artificial dialysis device or the dialyzed blood circulates, and used to analyze the condition of the blood.

Figure 6:
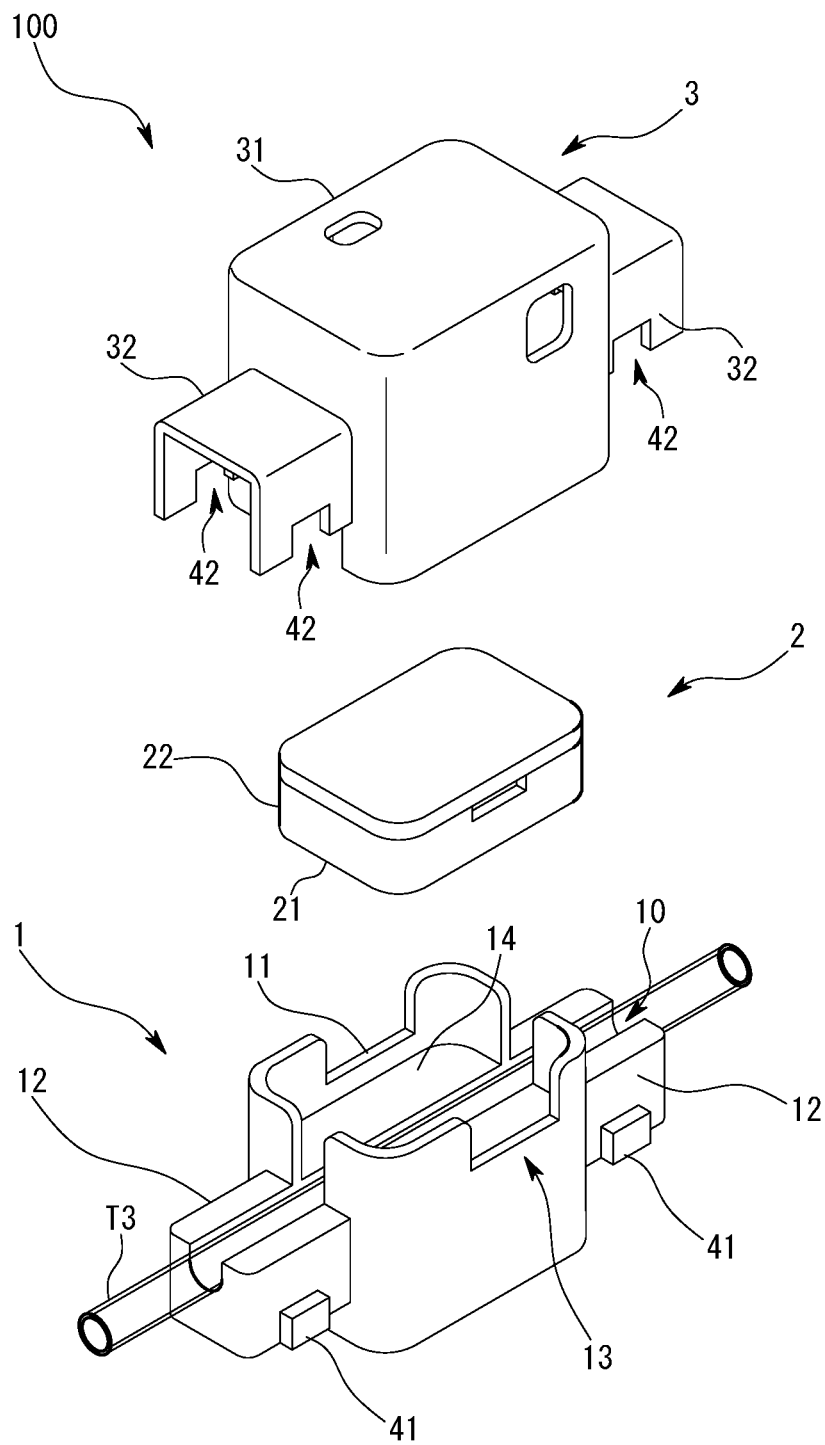
FIG. 6 is a schematic exploded perspective view of a body fluid analysis device according to a second embodiment of the present invention.
Figure 7:
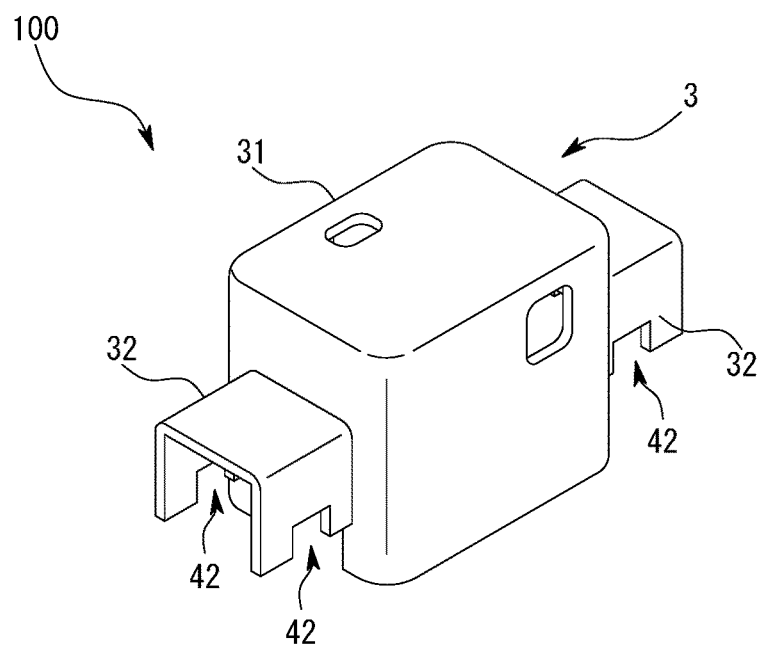
FIG. 7 is a schematic perspective view illustrating a state where an attachment is attached to a base of the body fluid analysis device according to the second embodiment of the present invention.
Figure 7:
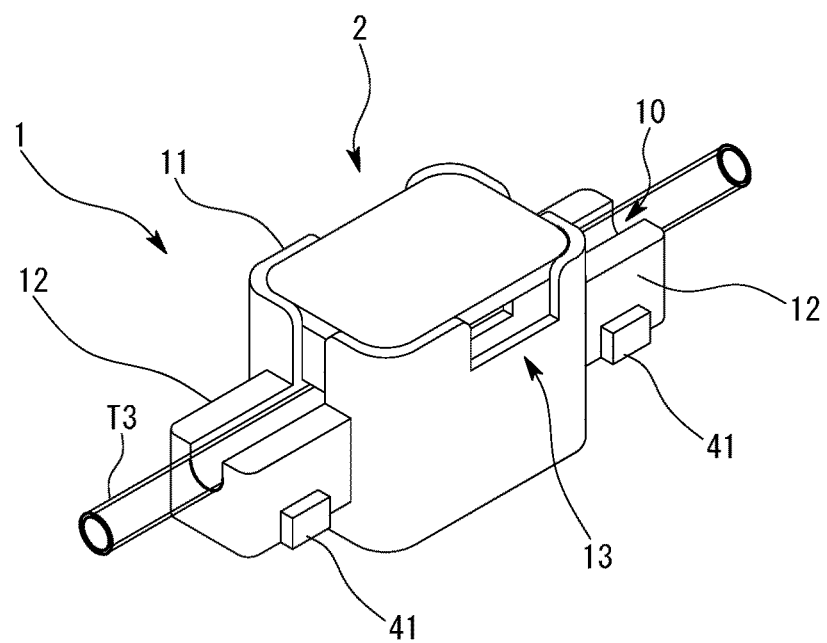
Figure 8:
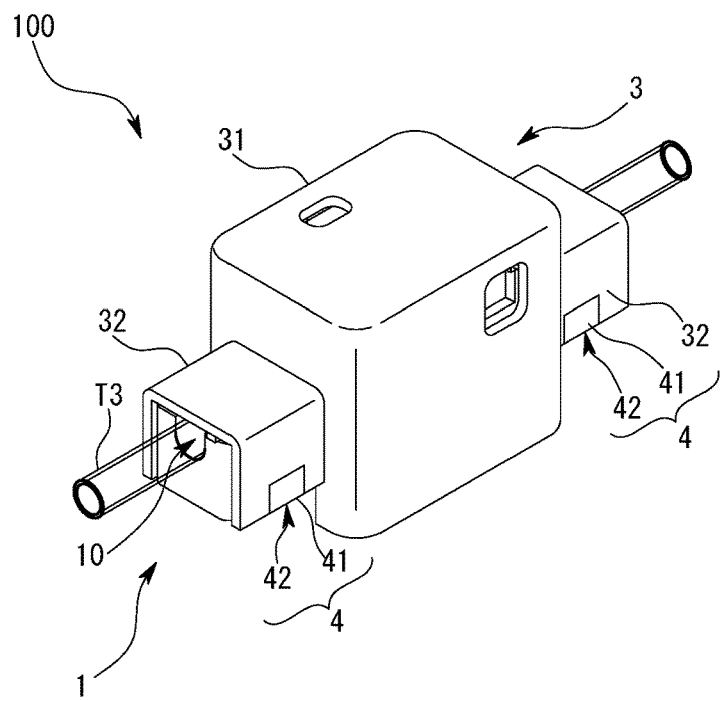
FIG. 8 is a schematic perspective view illustrating a state where the body fluid analysis device according to the second embodiment of the present invention is assembled.

As illustrated in FIG. 6 and FIG. 7, as compared with the body fluid analysis device 100 of the first embodiment, the body fluid analysis device 100 of the second embodiment is different in that the size of the groove 10 is set corresponding to the outside diameter of the blood transport tube T3 and in that the accommodation part 13 is configured to be able to accommodate the entire attachment 2.

Also, the body fluid analysis device 100 of the second embodiment is provided with a blood analysis part (not illustrated) in place of the urine analysis part 52, and configured to calculate an evaluation item such as the hematocrit value of blood on the basis of the output of the light receiving element D.

As described, even the body fluid analysis device 100 of the second embodiment can enjoy the same effect as that of the first embodiment in an artificial dialysis device.

Next, a body fluid analysis device 100 according to a third embodiment of the present invention will be described with reference to FIG. 9. In addition, members corresponding to the members described in the first embodiment will be marked with the same reference signs.

Figure 9:
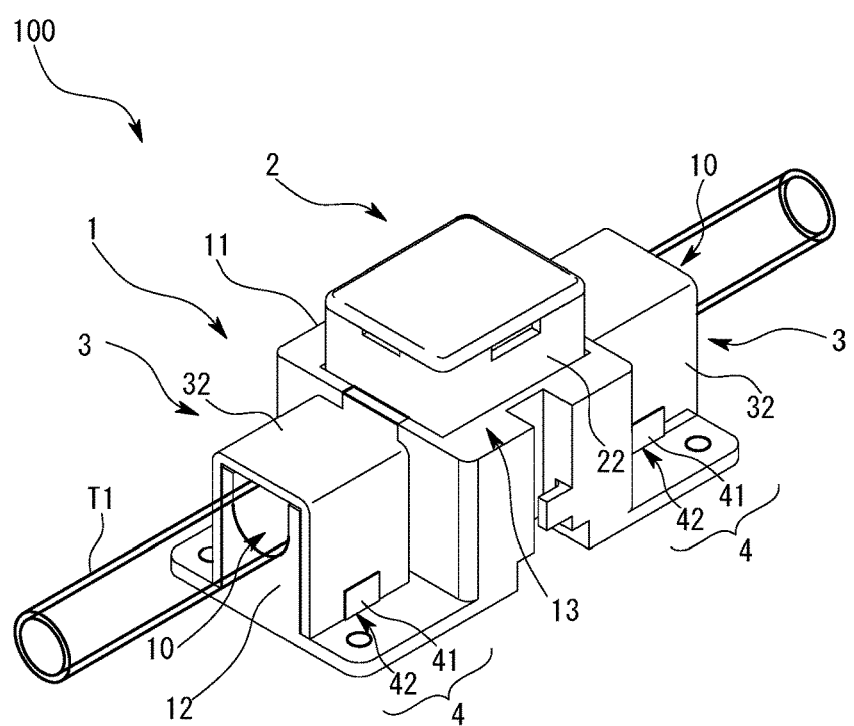
FIG. 9 is a schematic perspective view of a body fluid analysis device according to a third embodiment of the present invention.

As illustrated in FIG. 9, as compared with the body fluid analysis device 100 of the first embodiment, the body fluid analysis device 100 of the third embodiment is different in that the cover 3 does not include the pressing part that covers the main body part 11 and the attachment 2 attached to the main body part 11 and also presses them against the base 1, but includes only the shielding parts 32 that cover the protrusion parts 12.

Even the cover 3 configured as described makes it difficult for the light receiving element D to detect the outside light incident in the axial direction of the urine guide tube T1 and makes it possible to improve the analysis accuracy of urine. Also, by tightly setting the engagement of the attachment 2 with the accommodation part 13, the urine guide tube T1 can be sufficiently pinched even without being pressed by the cover 3. Further, since the urine guide tube T1 is provided between the attachment 2 and the main body part 11, this part can be adapted so that the outside light is prevented from entering in the radial direction without the cover 3.

Next, a body fluid analysis device 100 according to a fourth embodiment of the present invention will be described with reference to FIG. 10 and FIG. 11. In addition, members corresponding to the members described in the first embodiment will be marked with the same reference signs.

Figure 10:
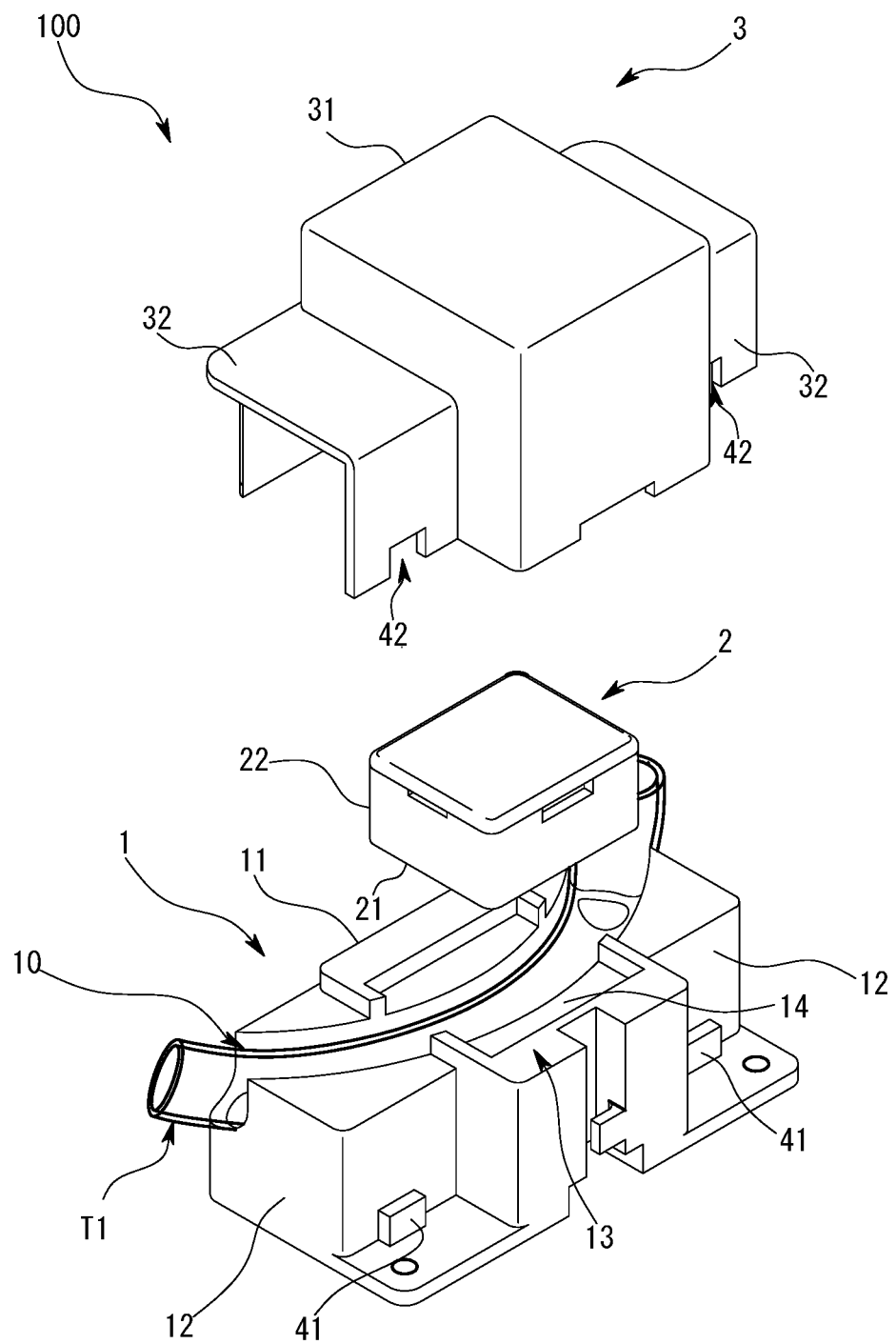
FIG. 10 is a schematic exploded perspective view of a body fluid analysis device according to a fourth embodiment of the present invention.

As illustrated in FIG. 10, as compared with the body fluid analysis device 100 of the first embodiment, the body fluid analysis device 100 of the fourth embodiment is different in that the groove 10 formed in the base 1 is not linearly but curvedly formed and in that the engagement protrusions 41 forming the engagement structures 4 are formed on only ones of the outer surfaces of the protrusion parts 12, and the engagement recess parts 42 are formed only in ones of the side surfaces of the shielding parts 32. The configuration of the groove 10 will be described below.

Figure 11:
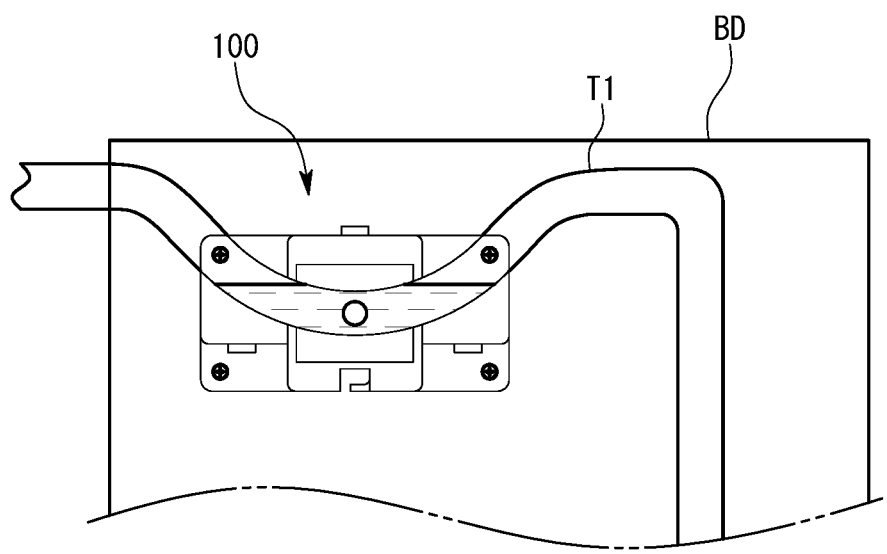
FIG. 11 is a schematic diagram illustrating a use state of the body fluid analysis device of the fourth embodiment.

As illustrated in FIG. 10 and FIG. 11, the groove 10 is formed in the base 1 so as to be formed in a substantially U-shape, and in a use state where light having passed through urine is received by the light receiving element D for analysis, the inflow side and outflow side of the urine guide tube T1 are respectively arranged at higher positions than the light axis of the light emitting element L.

That is, the groove 10 is curved so as to have the apex in the vicinity of the light axis of the light emitting element L. Also, as illustrated in FIG. 11, in the use state, installation is made so as to make the groove 10 downwardly convex, and the urine guide tube T1 is adapted so that urine is temporarily retained in a portion pinched between the main body part 11 of the base 1 and the attachment 2.

Since the groove 10 is curvedly provided as described, for example, even when the urine volume is small as in the case of elderly patients, the volume required to analyze urine is adapted to be constantly present in the vicinity of the light axis of the light emitting device L, making it possible to continuously analyze the urine. Also, urine can be prevented from flowing through the urine guide tube T1 at a flow rate having a predetermined value or more, and therefore an error can also be prevented from occurring in an analysis result because of the influence of the flow rate.

Other embodiments will be described.

The body fluid analysis device of the first embodiment is attached to the urine guide tube, but may be adapted to be attached to, for example, the outlet tube and analyze information such as the degree of occult blood in urine when draining the urine. Also, the body fluid analysis device may be adapted to measure an evaluation item other than the degree of occult blood on the basis of the output of the light receiving element. For example, it may be adapted to analyze a parameter that is detectable based on the transmitted light, such as the turbidity of urine.

The body fluid analysis device described in each of the embodiments is such that the base is provided with the light emitting element and the attachment is provided with the light receiving element; however, the base may be provided with the light receiving element and the attachment may be provided with the light emitting element. Also, the light emitting element may be adapted to be arranged in the through-hole of the base, and attached in contact with the outer surface of the tube. Further, each of the embodiments is configured so that any one of the base and the attachment is provided with the light emitting element or the light receiving element and the light emitting element and the light receiving element pinch the tube in the radial direction; however, one of the base and the attachment may be provided with the light emitting element and the light receiving element. In such a case, for example, it may be configured that the light emitted from the light emitting element is incident into the tube and reflected by the opposite side of the tube after passing through the body fluid, and the returning light is detected by the light receiving element. That is, a configuration may be made as a transmission type detector in which the light emitting element and the light receiving element pinch the tube or the configuration may be made as a reflection type detector in which the light emitting element and the light receiving element are arranged on the same side with respect to the outer surface of the tube. In addition, the configuration may be made as a transmission type detector in which the light emitting element and the light receiving element are both provided in the base and the light axis is set in the width direction of the groove.

The base of the body fluid analysis device may be one including only the main body part and provided with no protrusion part. In addition, the protrusion part may be provided on only one side of the main body part.

Further, the body fluid analysis device may be configured to include only the base and the attachment. In this case, an engagement structure may be configured between the base and the attachment, and it is preferable to provide light shielding so that, in a state where the attachment is attached, stray light is prevented from being incident on the optical system including the light emitting element and the light receiving element.

The shape of the groove is not limited to one curved in a U-shape as in the fourth embodiment, but only has to be curved so that the body fluid is temporarily retained in the vicinity of the main body part in the use state. For example, the groove may be formed so as to block the flow of the body fluid by making the inflow side of the tube horizontal and curving the outflow side of the tube upward. Further, the groove may be formed in a V-shape.

The body fluid analyzed by the body fluid analysis device is not limited to ones described in the first embodiment and the second embodiment. As the body fluid, lymph, interstitial fluid, cerebrospinal fluid, saliva, sweat, or the like is also acceptable. For example, a body fluid circulating through a drain attached to a patient during surgery or after surgery may be analyzed.

Besides, parts of various embodiments may be combined or part of each of the embodiments may be modified without departing from the scope of the present invention.

INDUSTRIAL APPLICABILITY

According to the present invention, it is possible to provide the body fluid analysis device that makes it possible to accurately and automatically classifying the condition of a body fluid in a tube on the basis of light even in the case of an index that is hard for a person to determine, such as the degree of occult blood.

The invention claimed is:

1. A body fluid analysis device that irradiates a body fluid in a tube having translucency with light and analyzes the body fluid on a basis of light having passed through the tube, the body fluid analysis device comprising:
   a base;
   an attachment that is attached to the base so that the tube is pinched in its radial direction between the attachment and the base;
   a light emitting element that is provided to the base or the attachment; and
   a light receiving element that is provided to the base or the attachment, wherein
   in a state where the attachment is attached to the base, between the base and the attachment, the light emitting element and the light receiving element are arranged so as to pinch the tube in the radial direction, or both of the light emitting element and the light receiving element are arranged together in one of the base and the attachment,
   the tube is pinched by the base and the attachment such that a shape of a curve of the tube is concave up in a vertical direction,
   the base includes a groove into which the tube is fitted,
   a path of the groove is formed in the base in a substantially U-shape such that the body fluid is temporarily retained in a portion of the tube at which a light axis of the light emitting element crosses, and
   in a use state in which the light receiving element is configured to receive the light having passed through the tube and the body fluid, the lowest point of an inflow side and the lowest point of an outflow side of the tube in the body fluid analysis device are higher than the light axis of the light emitting element.

2. The body fluid analysis device according to claim 1, wherein
   the attachment comprises a contact surface in contact with an outer surface of the tube, and
   the tube is configured to be pressed against the base in the state where the attachment is attached to the base.

3. The body fluid analysis device according to claim 2, wherein
   the attachment is configured so that at least a part of the light emitting element or the light receiving element is substantially flush with the contact surface.

4. The body fluid analysis device according to claim 1, wherein
   a through-hole for allowing light emitted from the light emitting element to pass is formed in a bottom part of the path of the groove.

5. The body fluid analysis device according to claim 4, wherein
   the base comprises:
      a main body part to which the attachment is attached; and
      a protrusion part that protrudes outward from the main body part along an extending direction of the groove and is formed with a part of the groove,
   the body fluid analysis device further comprising a cover that is configured to cover at least the protrusion part of the base.

6. The body fluid analysis device according to claim 5, further comprising
   an engagement structure formed between the base and the cover, wherein
   the cover is configured to cover the main body part of the base and the attachment attached to the main body part of the base, and
   the cover is configured to press the attachment against a base side in a state where the cover is engaged with the base by the engagement structure.

7. The body fluid analysis device according to claim 1, wherein
   the base comprises an accommodation part into which the attachment is fitted, and
   the light receiving element is configured to be arranged on the light axis of the light emitting element in a state where the attachment is fitted into the accommodation part.

8. The body fluid analysis device according to claim 1, wherein
   the path of the groove is formed so as to be concave up in the vertical direction in a use state where the light receiving element is made to receive the light having passed through the tube.

9. The body fluid analysis device according to claim 8, wherein
   the path of the groove is formed so as to have an apex in a vicinity of the light axis of the light emitting element in the main body part.

10. The body fluid analysis device according to claim 1, wherein
    urine flows through the tube,
    the body fluid analysis device further comprising a urine analysis part including a central processing unit (CPU), that analyzes the urine on a basis of an output of the light receiving element.

11. The body fluid analysis device according to claim 1, wherein
    blood flows through the tube, the body fluid analysis device further comprising a blood analysis part including a central processing unit (CPU), that analyzes the blood on a basis of an output of the light receiving element.

* * * * *